(12) United States Patent  
Riff

(10) Patent No.: US 8,961,505 B2  
(45) Date of Patent: Feb. 24, 2015

(54) ELECTROSURGERY DETECTION

(75) Inventor: Kenneth M. Riff, Wayzata, MN (US)

(73) Assignee: Medtronic, Inc., Minneapolis, MN (US)

( * ) Notice: Subject to any disclaimer, the term of this patent is extended or adjusted under 35 U.S.C. 154(b) by 556 days.

(21) Appl. No.: 13/337,877

(22) Filed: Dec. 27, 2011

(65) Prior Publication Data

US 2013/0165918 A1    Jun. 27, 2013

(51) Int. Cl.
*A61B 18/04* (2006.01)

(52) U.S. Cl.
USPC .......................................................... 606/34

(58) Field of Classification Search
USPC .......................................................... 606/34
See application file for complete search history.

(56) References Cited

U.S. PATENT DOCUMENTS 4,934,377 A    6/1990 Bova et al.
5,792,069 A *  8/1998 Greenwald et al. ........... 600/544
6,662,050 B2  12/2003 Olson
7,310,546 B2  12/2007 Prass
2010/0152806 A1  6/2010 Levine et al.

OTHER PUBLICATIONS

PowerPoint presentation by Luis S. Marsano, MD: "Principles of Electrocautery," University of Louisville & Louisville VAMC, accessed Oct. 18, 2011, 67 pp.
Eggleston, J. L., Von Maltzahn, W.W. "Electrosurgical Devices," The Biomedical Engineering Handbook: Second Edition, Ed. Joseph D. Bronzino, Boca Raton: CRC Press LLC, Chapter 81, 2000, 10 pp.

* cited by examiner

*Primary Examiner* — George Manuel
(74) *Attorney, Agent, or Firm* — Michael C. Soldner

(57) ABSTRACT

A device includes a plurality of electrodes and a detection module. The plurality of electrodes are configured to acquire an electrical signal in a patient. The detection module is configured to determine whether the acquired electrical signal includes signal content in each of N different frequency bands and detect operation of an electrosurgical device on the patient based on how many of the N different frequency bands include signal content. N is an integer that is greater than 1.

29 Claims, 7 Drawing Sheets

ELECTROSURGERY DETECTION

TECHNICAL FIELD

The disclosure relates to techniques for detecting operation of an electrosurgical device, and, more particularly, to detecting operation of an electrosurgical device based on the frequency content of signals generated by the electrosurgical device.

BACKGROUND

Electrosurgical devices may be used to perform a variety of different types of electrosurgical procedures on a patient. In general, electrosurgical devices may generate high frequency AC current that may be delivered to tissue of a patient via an electrode. The high frequency AC current may be used to cut, coagulate, fulgurate, ablate, and/or dessicate the tissue of the patient during a procedure. During an electrosurgical procedure, the patient may be included as part of the circuit such that current enters the patient's body and may travel through different paths in the patient's body depending on the type of procedure being performed and the placement of a return electrode. In some examples, an electrosurgical procedure may cause operational issues with medical devices attached to or implanted in the patient.

SUMMARY

Electrosurgical procedures may potentially interfere with operation of some implantable medical devices (IMDs), such as pacemakers and cardioverter-defibrillators. Prior to performing an electrosurgical procedure on a patient having an IMD, a clinician may reprogram the IMD in order to prevent potential issues that may arise in the IMD during the procedure. In examples where the IMD includes a pacemaker, the clinician may reprogram the IMD to an asynchronous pacing mode so that noise generated by the electrosurgical device (i.e., electrosurgical noise) may not cause inhibition of pacing. In examples where the IMD includes cardioverter-defibrillator functionality, the clinician may reprogram the IMD to disable arrhythmia detection and arrhythmia therapy so that electrosurgical noise generated by the electrosurgical device may not be interpreted as arrhythmias.

An IMD of the present disclosure may automatically detect operation of an electrosurgical device and transition into a safe operating mode that may not be affected by the electrosurgical noise caused by the electrosurgical device. For example, the IMD of the present disclosure may pick up electrosurgical noise generated by an electrosurgical device via electrodes, detect the electrosurgical noise, and transition to the safe operating mode in order to prevent interpretation of the electrosurgical noise as physiological electrical signals (e.g., cardiac electrical signals). In general, the IMD may detect electrosurgical noise when the IMD determines that a plurality of different frequency bands include greater than a threshold amount of signal content. The frequency bands monitored by the IMD may be selected such that the frequency bands may include electrosurgical noise but tend not to include physiological electrical signals and other types of physiological and non-physiological noise other than the electrosurgical noise.

Automatic detection of electrosurgical noise by the IMD of the present disclosure may eliminate the need to reprogram the IMD prior to an electrosurgical procedure, and may also eliminate the need to reprogram the IMD to its prior state once the electrosurgical procedure is finished. Accordingly, the IMD of the present disclosure may provide a more efficient workflow for clinicians performing electrosurgical procedures on patients having IMDs.

In some examples according to the present disclosure, a device comprises a plurality of electrodes and a detection module. The pluralities of electrodes are configured to acquire an electrical signal in a patient. The detection module is configured to determine whether the acquired electrical signal includes signal content in each of N different frequency bands and detect operation of an electrosurgical device on the patient based on how many of the N different frequency bands include signal content. N is an integer that is greater than 1.

In some examples according to the present disclosure, a method comprises acquiring an electrical signal in a patient using a plurality of electrodes, determining whether the acquired electrical signal includes signal content in each of N different frequency bands, and detecting operation of an electrosurgical device on the patient based on how many of the N different frequency bands include signal content. N is an integer that is greater than 1.

In some examples according to the present disclosure, a device comprises a plurality of electrodes, N band-pass filters, N comparison modules, and a content detection module. The pluralities of electrodes are configured to acquire an electrical signal in a patient. The N band-pass filters are configured to filter the acquired electrical signal to generate N filtered signals. The N comparison modules are each configured to receive a different one of the N filtered signals and indicate whether the received signal includes greater than a threshold amount of signal content. The content detection module detects operation of an electrosurgical device on the patient based on how many of the N comparison modules indicate that the received signal includes greater than a threshold amount of signal content. N is an integer that is greater than 1.

The details of one or more examples are set forth in the accompanying drawings and the description below. Other features, objects, and advantages will be apparent from the description and drawings, and from the claims.

DETAILED DESCRIPTION

Figure 1:
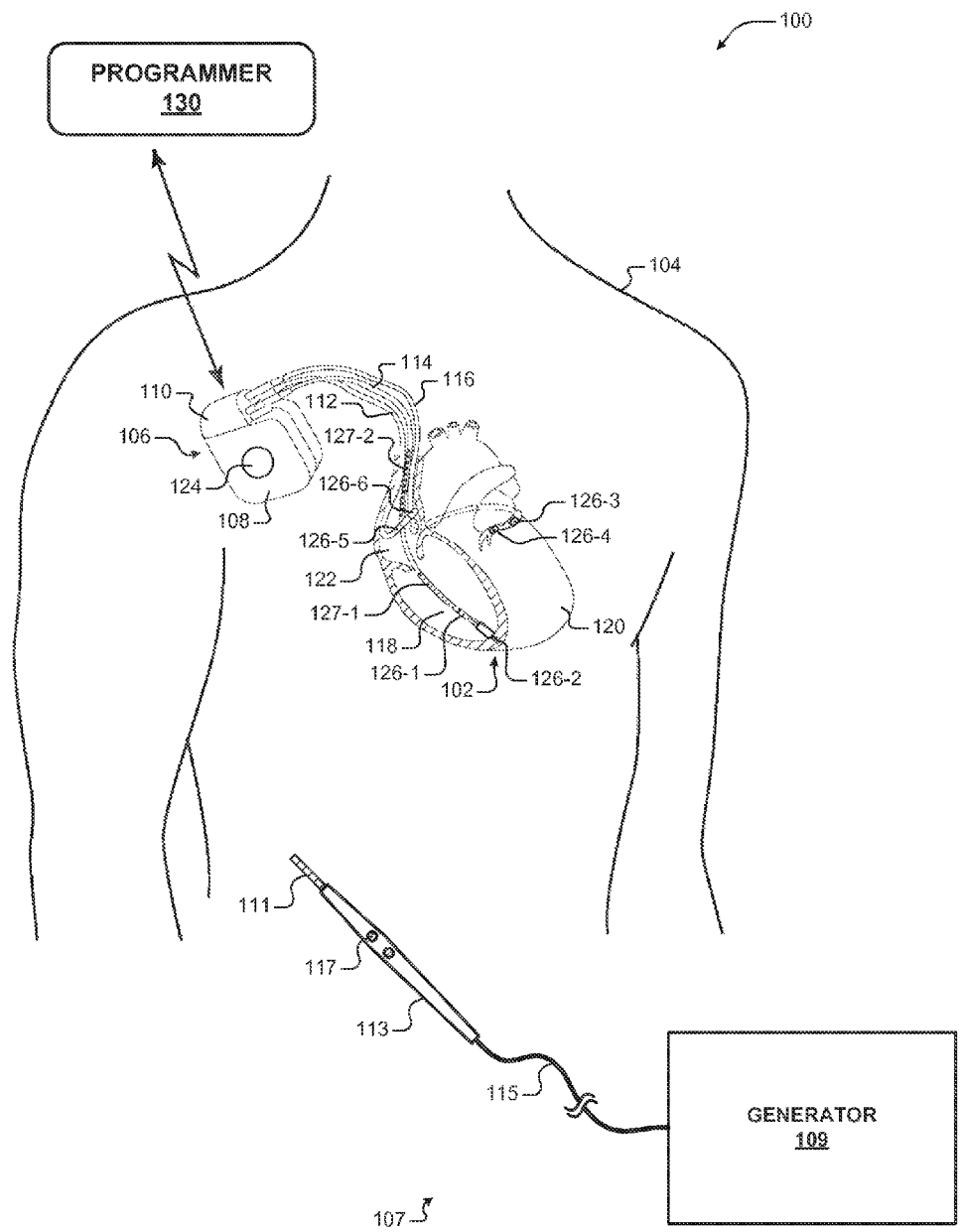
FIG. 1 shows an electrosurgical device operating on a patient having an implantable medical device (IMD) that detects operation of the electrosurgical device.

Electrosurgical devices may be used to perform a variety of different types of electrosurgical procedures on a patient. In general, electrosurgical devices may generate high frequency AC current that may be delivered to tissue of patient via an electrode. The high frequency AC current may be used to cut, coagulate, fulgurate, ablate, and/or dessicate tissue of the patient during a procedure. In general, the term "electrosurgery" may be used herein to describe surgical procedures that use high frequency AC current in order to cut, coagulate, fulgurate, ablate, and/or dessicate patient tissue. Electrosurgery may involve the generation of high frequency AC current, e.g., radio frequency (RF) current at frequencies of 100 kHz and above. During an electrosurgical procedure, the patient may be included as part of the circuit such that current enters the patient's body and may travel through different paths in the patient's body depending on the type of procedure being performed and the placement of a return electrode.

In some examples, the term "electrocautery" may be used interchangeably with the term "electrosurgery." Accordingly, an electrosurgical device described herein may sometimes be referred to generally as an "electrocautery device." During operation of an electrosurgical device, (e.g., while delivering high frequency AC current), the high frequency AC current delivered to the tissue of the patient may generate electrical noise signals in the patient. The electrical noise generated in the patient during operation of the electrosurgical device may be referred to herein as "electrosurgical noise." Electrosurgical noise may exhibit a power spectrum including a wide range of frequency content that is not typically generated in a patient's body via a physiological processes. For example, electrosurgical noise may include high-frequency content (e.g., RF content in the range of approximately 450 kHz to 5 MHz) that may not be produced in the body via physiological processes. Electrosurgical noise generated during operation of the electrosurgical device may not be limited to a narrow high-frequency band (e.g., an RF band), but may also include a wide range of frequency content that is outside of the narrow RF band generated by the electrosurgical device. For example, the electrosurgical noise generated in the patient may include a wide frequency band, e.g., similar to that of "white noise," in that the frequency content of the electrosurgical noise may include content that extends into lower frequency ranges (e.g., from approximately 10 Hz to 20 kHz). Such a wide range of frequency content included in the electrosurgical noise may also not be physiologically producible. Furthermore, the power of the electrosurgical noise at frequencies that overlap with physiological electrical signals may be greater than the power of the physiological signals at those overlapping frequencies. In summary, the electrosurgical device may generate electrosurgical noise that 1) includes high frequency content that may not be physiologically producible, 2) includes a wide range of frequency content that may not be physiologically producible, and 3) may include greater power at those frequencies which overlap with physiological electrical signals.

Some implantable medical devices (IMDs) implanted in patients may pick up electrosurgical noise (e.g., via electrodes). For example, an IMD implanted in a patient may pick up electrosurgical noise when the patient is undergoing an electrosurgical procedure, e.g., when the patient is having tissue cut, coagulated, etc., with an electrosurgical device. The electrosurgical noise picked up by an IMD may cause various issues in the IMD, depending on the type of IMD that is implanted. As described herein, an IMD may include a pacemaker and/or cardioverter-defibrillator (ICD). When the IMD includes a pacemaker, the electrosurgical noise generated by the electrosurgical device may cause the IMD to incorrectly detect sensed cardiac beats, which may inhibit pacing, depending on the mode of the pacemaker. In examples where the IMD includes a cardioverter-defibrillator, the electrosurgical noise generated by the electrosurgical device may cause the IMD to incorrectly detect an arrhythmia, which may cause the IMD to inappropriately deliver therapy. Although electrosurgical noise may cause issues in implantable pacemaker and cardioverter-defibrillator devices, as described herein, it is contemplated that electrosurgical noise may cause issues in other types of medical devices, such as neurostimulation devices that may be used to stimulate targets that include, but are not limited to, spinal cord targets, deep brain stimulation (DBS) targets, gastric nerves, pelvic nerves, peripheral nerves, and/or a variety of organs, such as the stomach, bladder, or the like.

An IMD (e.g., pacemaker and/or ICD) of the present disclosure may detect operation of an electrosurgical device and transition to an operating mode that prevents any operational issues that the IMD may potentially encounter when subjected to electrosurgical noise. For example, the IMD of the present disclosure may pick up electrosurgical noise via electrodes (e.g., on leads or on the housing), detect the electrosurgical noise, and transition to a different mode of operation in response to detection of the electrosurgical noise in order to prevent interpretation of the electrosurgical noise as physiological electrical signals (e.g., cardiac electrical signals).

The IMD of the present disclosure may implement one or more techniques to detect electrosurgical noise generated by an electrosurgical device. Generally, the IMD may detect electrosurgical noise when the IMD determines that a plurality of different frequency bands include greater than a threshold amount of signal content. The frequency bands monitored by the IMD may be selected such that the frequency bands may include electrosurgical noise but tend not to include physiological electrical signals (and other types of physiological and non-physiological noise other than electrosurgical noise). For example, one or more of the monitored frequency bands may include high frequency content (e.g., RF frequency content) that may not be physiologically producible. Additionally, or alternatively, the monitored frequency bands may be selected such that the bands include a wide range of frequency content, e.g., outside the range of frequency content that is typically produced physiologically, or via other noise sources.

The threshold amount of signal content associated with each frequency band may be selected such that an amount of signal content above the threshold amount may be greater than that which is generated physiologically, and instead may be more indicative of electrosurgical noise. In some examples, the monitored frequency bands may include frequency content of both physiological electrical signals and electrosurgical noise. In these examples, the IMD may determine that the signal content at the overlapping frequencies is due to electrosurgical noise based on the thresholds associated with the frequencies. For example, in overlapping frequencies, the electrosurgical noise may tend to have a greater amount of signal content (e.g., power/amplitude) than may produced physiologically.

The IMD may acquire various electrical signals via electrodes. Typically, the electrical signals acquired via the electrodes include physiological electrical signals, such as cardiac electrical activity, or other electrical physiological signals. In some examples, the signals acquired via the electrodes include non-physiological noise such as grid power in the range of 50-60 Hz, or other signals generated by other medical devices attached to the patient or implanted in the patient. In scenarios where an electrosurgical device is operating on the patient having the IMD, the electrodes of the IMD may pick up electrosurgical noise via the electrodes. In some examples described herein, the IMD may additionally, or alternatively, pick up electrosurgical noise via an internal antenna of the IMD.

The IMD may detect the electrosurgical noise and determine that an electrosurgical device is in operation, e.g., on or near tissue of the patient, based on detection of electrical signals having a threshold amount of signal content in a plurality of different frequency bands. The IMD may determine whether electrical signals are present in a number of different frequency bands and detect operation of an electrosurgical device based on the number of different frequency bands that include components of the acquired electrical signal. In other words, the IMD may detect electrosurgical noise in response to detection of a threshold amount of signal content in a threshold number of different frequency bands.

In some examples, the IMD may amplify the electrical signals acquired by the electrodes. The IMD may then determine whether a threshold amount of signal content is present in each of a plurality of different frequency bands. The plurality of different frequency bands may be described herein as N different frequency bands, wherein N is an integer that is greater than one. As described herein, the N different frequency bands may be frequency bands that have N different center frequencies. In some examples, the N different frequency bands may have passbands that are separated from one another. In other examples, the passbands may overlap along the edges of the passbands. The center frequencies and the widths of the passbands of the N different frequency bands may be selected as described above. For example, the center frequencies and passband widths of the N frequency bands monitored by the IMD may be selected such that the N frequency bands may include electrosurgical noise but tend not to include physiological electrical signals. In some examples, one or more of the N monitored frequency bands may include high frequency content (e.g., RF frequency content) that may not be physiologically producible. In some examples, one or more of the center frequencies and the passband widths of the N monitored frequency bands may be selected such that the bands include a wide range of frequency content, e.g., outside the range of frequency content that is typically produced physiologically, or via other noise sources.

The IMD may determine whether a threshold amount of signal content is present in each of the N different frequency bands using a variety of different signal analysis techniques. In some examples, the IMD may perform frequency domain analysis on the acquired signals to determine whether a threshold amount of signal content is present in each of the N different frequency bands. For example, the IMD may perform frequency domain analysis to determine whether the power of the acquired signals in each of the N different frequency bands is greater than a threshold power. In other examples, the IMD may perform analysis on the acquired signals in the time domain to determine whether a threshold amount of signal content is present in each the N different frequency bands. For example, the IMD may filter the acquired signals using a plurality of different filters having passbands corresponding to the N different frequency bands, and then the IMD may perform a threshold analysis (e.g., peak detection) on the filtered signals. In this example, the IMD may determine that a threshold amount of signal content is present in a frequency band when the filtered signal has an amplitude (e.g., peak, or peak-peak) that is greater than a threshold voltage, for example.

The IMD of the present disclosure may detect operation of an electrosurgical device based on how many of the N different frequency bands include a threshold amount of signal content. The IMD may detect operation of an electrosurgical device when the number of the N different frequency bands that include a threshold amount of signal content is greater than the threshold number of bands. In some examples, the IMD may detect operation of an electrosurgical device if only two of the N different frequency bands include a threshold amount of signal content. In other examples, the IMD may detect operation of an electrosurgical device only when more than two of the N different frequency bands include a threshold amount of signal content. In some examples, the IMD may require all of the N different frequency bands to include a threshold amount of signal content for the IMD to detect operation of an electrosurgical device.

The IMD of the present disclosure may change operating mode when the IMD detects operation of an electrosurgical device. For example, when the IMD includes pacing functionality, the IMD may change pacing mode to an asynchronous pacing mode in which pacing stimuli are unrelated to a sensed rhythm (e.g., VOO mode) so that noise generated by the electrosurgical device may not cause inhibition of pacing. In examples where the IMD includes cardioverter-defibrillator functionality, the IMD may disable arrhythmia detection and arrhythmia therapy so that electrosurgical noise may not be interpreted as arrhythmias, thereby preventing inappropriate detection of arrhythmias and a potential inappropriate delivery of therapy.

The IMD of the present disclosure may include various parameters that a user may configure in order to customize detection of an electrosurgical device. In some examples, parameters associated with the N different frequency bands may be configurable. For example, the center frequencies of the N different frequency bands may be configurable. Additionally, or alternatively, the widths of the passbands of each of the N different frequency bands may be configurable. As described above, the IMD may determine whether a threshold amount of signal content is present in each of the N different frequency bands. In some examples, the threshold amounts associated with each of the N different frequency bands may be configurable, such that some of the N different frequency bands may be associated with greater or lesser thresholds than other frequency bands.

Techniques for detecting operation of an electrosurgical device are described hereinafter with respect to FIGS. 1-7. Use of an electrosurgical device on a patient having an IMD (e.g., pacemaker, cardioverter, and/or defibrillator) is illustrated and described herein with respect to FIG. 1. Detailed description of an example IMD that detects operation of the electrosurgical device is described hereinafter with respect to FIGS. 1-6. Functional block diagrams of an example IMD configured to detect operation of an electrosurgical device are illustrated in FIGS. 2-6. An example method for detecting operation of an electrosurgical device is described with respect to FIG. 7.

FIG. 1 shows an example system 100 that may be used to diagnose conditions of and provide therapy to a heart 102 of a patient 104. System 100 includes an IMD 106 that may detect operation of an electrosurgical device 107. For example, IMD 106 may be an implantable pacemaker, cardioverter, and/or defibrillator that monitors electrical activity of heart 102 and provides electrical stimulation to heart 102. Although IMD 106 is illustrated and described herein as an implantable pacemaker, cardioverter, and/or defibrillator, it is contemplated that other implantable or external devices may be configured to detect operation of an electrosurgical device according to the techniques of the present disclosure. Other devices that may detect operation of an electrosurgical device may include implantable devices such as neurostimulation devices.

Electrosurgical device 107 may be used to perform electrosurgical procedures on patient 104. Electrosurgical device 107 may generate high frequency AC current that may be delivered to tissue of patient 104 in order to cut, coagulate, fulgurate, ablate, and/or dessicate tissue of patient 104. The term "electrosurgery" is used herein to describe surgical procedures that use high frequency AC current in order to cut, coagulate, fulgurate, ablate, and/or dessicate patient tissue. Electrosurgery may involve the generation of high frequency AC current, e.g., radio frequency (RF) current. In some examples, the RF current may be generated at frequencies of 100 kHz and above. During an electrosurgical procedure, patient 104 may be included as part of the circuit such that current enters the patient's body and may travel through different paths in the patient's body depending on the type of procedure being performed and the placement of a return electrode.

Electrosurgical device 107 includes a generator 109 that delivers high frequency AC current to an electrode 111 that, in the illustrated example, is coupled to a surgical pencil 113 via cord 115. Surgical pencil 113 may be manipulated by a clinician in order to perform surgery on patient 104. Electrode 111 may deliver the AC current to the tissue of patient 104 in order to cut and coagulate tissue of patient 104. In some examples, electrosurgical device 107 may include a return electrode (not shown) that may be attached to patient 104 to provide a return path for the high frequency current delivered by electrode 111 to patient 104. Electrode 111 may be selected from a number of different types of electrodes, depending on the surgical procedure for which electrode 111 will be used. For example, electrode 111 may be a blade electrode, a needle electrode, a ball electrode, a loop electrode, forceps electrodes, or an arthroscopic electrode. In some examples, electrode 111 may be attached to a catheter or other mechanism to position electrode 111 within patient 104.

Generator 109 may generate the high frequency AC current delivered by electrode 111 to patient 104. Generator 109 may provide a variety of different waveforms to electrode 111 in order to modify the effect that electrode 111 has on the tissue of patient 104. For example, generator 109 may generate AC current according to different waveforms to cause cutting, coagulation, fulguration, ablation, and/or dessication. In some examples, generator 109 may operate in different modes, e.g., either a monopolar mode or a bipolar mode.

Generator 109 may include controls that allow the clinician to select different settings for the electrosurgical procedure. For example, generator 109 may include various switches and knobs that the clinician may use to set parameters for delivery of AC current via electrode 111 to control the power delivered during the procedure and the waveform delivered during the procedure. Various controls may also be available on surgical pencil 113 for controlling delivery of high frequency AC current during an electrosurgical procedure. For example, surgical pencil 113 may include control buttons 117 which may be used by the clinician in order to turn the high frequency AC delivery on/off and in order to select the type of waveform delivered (e.g., cut, coagulate, etc.). In some examples, foot pedal controls (not shown) may be connected to generator 109 and used by a clinician in order to turn the high frequency AC delivery on/off and in order to select the type of waveform delivered via electrode 111.

When electrosurgical device 107 is in operation, e.g., delivering high frequency AC current to tissue of patient 104, the high frequency AC current delivered to the tissue of patient 104 by electrode 111 may generate electrosurgical noise in patient 104 that may be acquired by electrodes of IMD 106. As described above, electrosurgical noise may exhibit a power spectrum that is not typically generated in a patient's body via a physiological process. IMD 106 may detect the presence of electrosurgical noise. For example, IMD may detect electrosurgical noise when IMD 106 determines that acquired electrical signals have greater than a threshold amount of signal content at a plurality of different frequency bands which typically do not include physiological electrical activity detected by IMD 106.

Although electrosurgical device 107 is illustrated as including generator 109, surgical pencil 113, and an electrode 111, it is contemplated that the techniques of the present disclosure may be applicable to detecting other configurations of electrosurgical devices. As described above, in some examples, the term "electrocautery" may be used interchangeably with the term "electrosurgery." Accordingly, it is contemplated that the techniques of the present disclosure may be implemented in an IMD to detect devices referred to as "electrocautery devices." Additionally, it is contemplated that the techniques of the present disclosure may be implemented in an IMD in order to detect any other medical device that generates noise that may exhibit a power spectrum including a wide range of frequency content that is not typically generated in a patient's body via physiological processes. For example, the techniques of the present disclosure may be implemented in an IMD in order to detect surgical diathermy procedures, ablation procedures (e.g., RF ablation procedures), etc.

IMD 106 includes a housing 108 and a connector block 110. IMD 106 is coupled to leads 112, 114, and 116 via connector block 110. Leads 112, 114, 116 extend into heart 102. Right ventricular lead 114 extends into right ventricle 118. Left ventricular coronary sinus lead 116 extends into the coronary sinus to a region adjacent to the free wall of left ventricle 120. Right atrial lead 112 extends into right atrium 122.

Housing 108 may enclose an electrical sensing module that monitors electrical activity of heart 102, and may also enclose a signal generator module that generates therapeutic stimulation, such as cardiac pacing pulses, ATP therapy, cardioversion therapy, and/or defibrillation therapy. Leads 112, 114, 116 are coupled to the signal generator module and the electrical sensing module of IMD 106 via connector block 110.

IMD 106 includes a housing electrode 124, which may be formed integrally with an outer surface of housing 108 of IMD 106 or otherwise coupled to housing 108. Although a single housing electrode 124 is illustrated in FIG. 1, IMD 106 may include more or less than a single housing electrode 124. Leads 112, 114, 116 include electrodes 126-1 to 126-6 (collectively "electrodes 126"). Lead 114 includes bipolar electrodes 126-1, 126-2 which are located in right ventricle 118. Lead 116 includes bipolar electrodes 126-3, 126-4 which are located in the coronary sinus. Lead 112 includes bipolar electrodes 126-5, 126-6 which are located in right atrium 122. Electrodes 126-1, 126-3, 126-5 may take the form of ring electrodes. Electrodes 126-2, 126-4, 126-6 may take the form of, for example, helix tip electrodes or small circular electrodes at the tip of a tined lead or other fixation element. Lead 114 includes elongated electrodes 127-1, 127-2 (collectively "electrodes 127") which may be coil electrodes. Electrode 127-1 may be referred to as HVB electrode 127-1 or as a right ventricular coil (RVC) electrode, and electrode 127-2 may be referred to as HVX electrode 127-2 or as a superior vena cava (SVC) coil electrode. Although three leads 112, 114, 116 are illustrated, systems according to the present disclosure may be implemented using more or less than 3 leads. Additionally, systems according to the present disclosure may be implemented using additional or fewer electrodes than illustrated in FIG. 1.

IMD 106 may sense electrical activity of heart 102 and/or deliver electrical stimulation to heart 102 via electrodes 124, 126, 127. IMD 106 may sense electrical activity using any combination of electrodes 124, 126, 127. For example, IMD 106 may sense electrical activity via any bipolar combination of electrodes 126, 127. Furthermore, any of electrodes 126, 127 may be used for unipolar sensing in combination with housing electrode 124. IMD 106 may deliver pacing pulses using a unipolar or bipolar combination of electrodes 124, 126, 127. IMD 106 may deliver high-energy therapy (e.g., cardioversion pulses and/or defibrillation pulses) to heart 102 via any combination of elongated electrodes HVB 127-1, HVX 127-2, and housing electrode HVA 124.

Using the signal generator module and the electrical sensing module, IMD 106 may provide pacing pulses to heart 102 based on the electrical signals sensed within heart 102. IMD 106 may also provide ATP therapy, cardioversion, and/or defibrillation therapy to heart 102 based on the electrical signals sensed within heart 102. For example, IMD 106 may detect an arrhythmia of heart 102, such as VT/VF, and deliver ATP therapy, cardioversion, or defibrillation therapy to heart 102 in response to the detection of VT/VF.

System 100 may include a programmer 130. Programmer 130 may be a handheld computing device, desktop computing device, a networked computing device, etc. Programmer 130 may include a computer-readable storage medium having instructions that cause a processor of programmer 130 to provide the functions attributed to programmer 130 in the present disclosure. In some examples, programmer 130 may include a telemetry head (not shown). IMD 106 and programmer 130 may wirelessly communicate with one another, e.g., transfer data between one another, using the telemetry head in some examples. For example, IMD 106 may send data to programmer 130, and programmer 130 may retrieve data stored in IMD 106 and/or program IMD 106.

Data retrieved from IMD 106 using programmer 130 may include cardiac electrograms (EGMs) stored by IMD 106 that indicate electrical activity of heart 102 and marker channel data that indicates the occurrence and timing of sensing, diagnosis, and therapy events associated with IMD 106. Data transferred to IMD 106 using programmer 130 may include, for example, values for operational parameters of IMD 106, and configurable parameters used for electrosurgical device detection.

Figure 2:
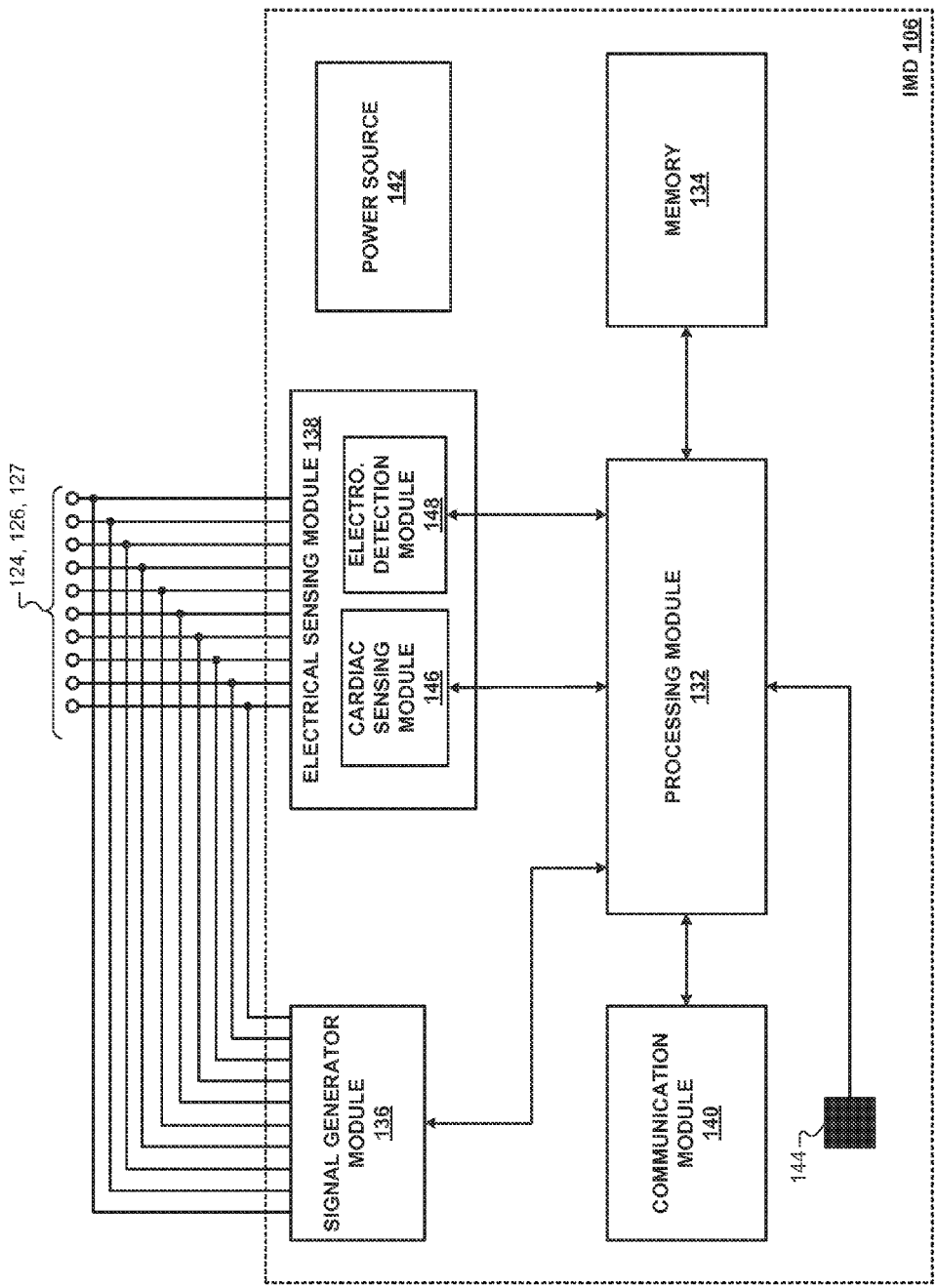
FIG. 2 shows a functional block diagram of an example IMD that detects operation of an electrosurgical device.

FIG. 2 shows a functional block diagram of an example IMD 106. IMD 106 includes a processing module 132, memory 134, a signal generator module 136, an electrical sensing module 138, a communication module 140, and a power source 142, such as a battery, e.g., a rechargeable or non-rechargeable battery. In some examples, IMD 106 may include one or more sensors (e.g., sensor 144) with which processing module 132 may communicate. For example, sensor 144 may comprise at least one of a motion sensor (e.g., an accelerometer or piezoelectric element), a hemodynamic pressure sensor, and a heart sound sensor. Processing module 132 may determine, for example, an activity level of patient 104, a hemodynamic pressure of patient 104, and a heart rate of patient 104 based on data measured by sensor 144.

Modules included in IMD 106 represent functionality that may be included in IMD 106 of the present disclosure. Modules of the present disclosure may include any discrete and/or integrated electronic circuit components that may be used to implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Processing module 132 may communicate with memory 134. Memory 134 may include computer-readable instructions that, when executed by processing module 132, cause processing module 132 to perform the various functions attributed to processing module 132 herein. Memory 134 may include any volatile, non-volatile, magnetic, or electrical media, such as RAM, ROM, NVRAM, EEPROM, Flash memory, or any other digital media. In some examples, memory 134 may include settings for electrosurgery detection, e.g., thresholds, frequency characteristics, etc. Processing module 132 may retrieve the settings and program the settings into electrosurgery detection module 148, or otherwise configure electrosurgery detection module 148 based on the settings.

Processing module 132 may communicate with signal generator module 136 and electrical sensing module 138. Signal generator module 136 and electrical sensing module 138 are electrically coupled to electrodes 126, 127 of leads 112, 114, 116 and housing electrode 124. In general, electrical sensing module 138 may acquire electrical signals (e.g., cardiac electrical signals and electrosurgical noise) via any of electrodes 124, 126, 127, detect cardiac electrical activity based on the acquired electrical signals, and detect operation of electrosurgical device 107 (i.e., electrosurgical noise) based on the acquired electrical signals.

Electrical sensing module 138 includes a cardiac sensing module 146 and an electrosurgery detection module 148. Cardiac sensing module 146 is configured to monitor signals acquired via electrodes 124, 126, 127 in order to monitor electrical activity of heart 102. Cardiac sensing module 146 may selectively monitor any bipolar or unipolar combination of electrodes 124, 126, 127. Cardiac sensing module 146 may include signal conditioning circuits, e.g., amplification and filtering circuits that amplify and filter cardiac electrical signals received from electrodes 124, 126, 127. Cardiac sensing module 146 may include analog-to-digital (A/D) conversion circuits that digitize the conditioned cardiac electrical signals to generate raw digital data. In some examples, the A/D circuits may include an 8 bit A/D converter that samples conditioned cardiac electrical signals at approximately 256 Hz. Processing module 132 may receive raw data from cardiac sensing module 146. Processing module 132 may sense events (e.g., ventricular contractions) based on the raw data and may analyze the raw data and detect arrhythmias (e.g., VT/VF) using any suitable arrhythmia detection algorithm. For example, processing module 132 may monitor the length of intervals between sensed ventricular events, and detect arrhythmias (e.g., VT/VF) when a predetermined number of those intervals are shorter than a programmed time interval.

Electrosurgery detection module 148 may detect the presence of electrosurgical noise. For example, electrosurgery detection module 148 may detect the presence of electrosurgical noise when the electrical signals acquired via any combination of electrodes 124, 126, 127 include greater than a threshold amount of signal content at a plurality of different frequency bands which typically do not include physiological electrical activity detected via electrodes 124, 126, 127 when electrosurgical device 107 is not in operation. Electrosurgery detection module 148 is described in greater detail hereinafter with respect to FIGS. 3-7.

Signal generator module 136 may generate and deliver electrical stimulation therapy to heart 102 via electrodes 124, 126, 127. Electrical stimulation therapy may include at least one of pacing pulses, ATP therapy, cardioversion therapy, and defibrillation therapy. Processing module 132 may control signal generator module 136 to deliver electrical stimulation therapy to heart 102 according to one or more therapy programs, which may be stored in memory 134. For example, processing module 132 may control signal generator module 136 to deliver pacing pulses to heart 102 based on one or more therapy programs and signals received from cardiac sensing module 146. In other examples, processing module 132 may control signal generator module 136 to deliver at least one of ATP therapy, cardioversion therapy, and defibrillation therapy when processing module 132 detects a tachyarrhythmia. For example, in the event that processing module 132 detects a tachyarrhythmia, processing module 132 may load an ATP regimen from memory 134, and control signal generator module 136 to implement the ATP regimen. In other examples, processing module 132 may implement a cardioversion regimen or a defibrillation regimen upon detection of a tachyarrhythmia.

Communication module 140 includes any suitable hardware, firmware, software or any combination thereof for communicating with another device, such as programmer 130 and/or a patient monitor. Under the control of processing module 132, communication module 140 may receive downlink telemetry from and send uplink telemetry to programmer 130 and/or a patient monitor with the aid of an antenna (not shown) in IMD 106.

Figure 3:
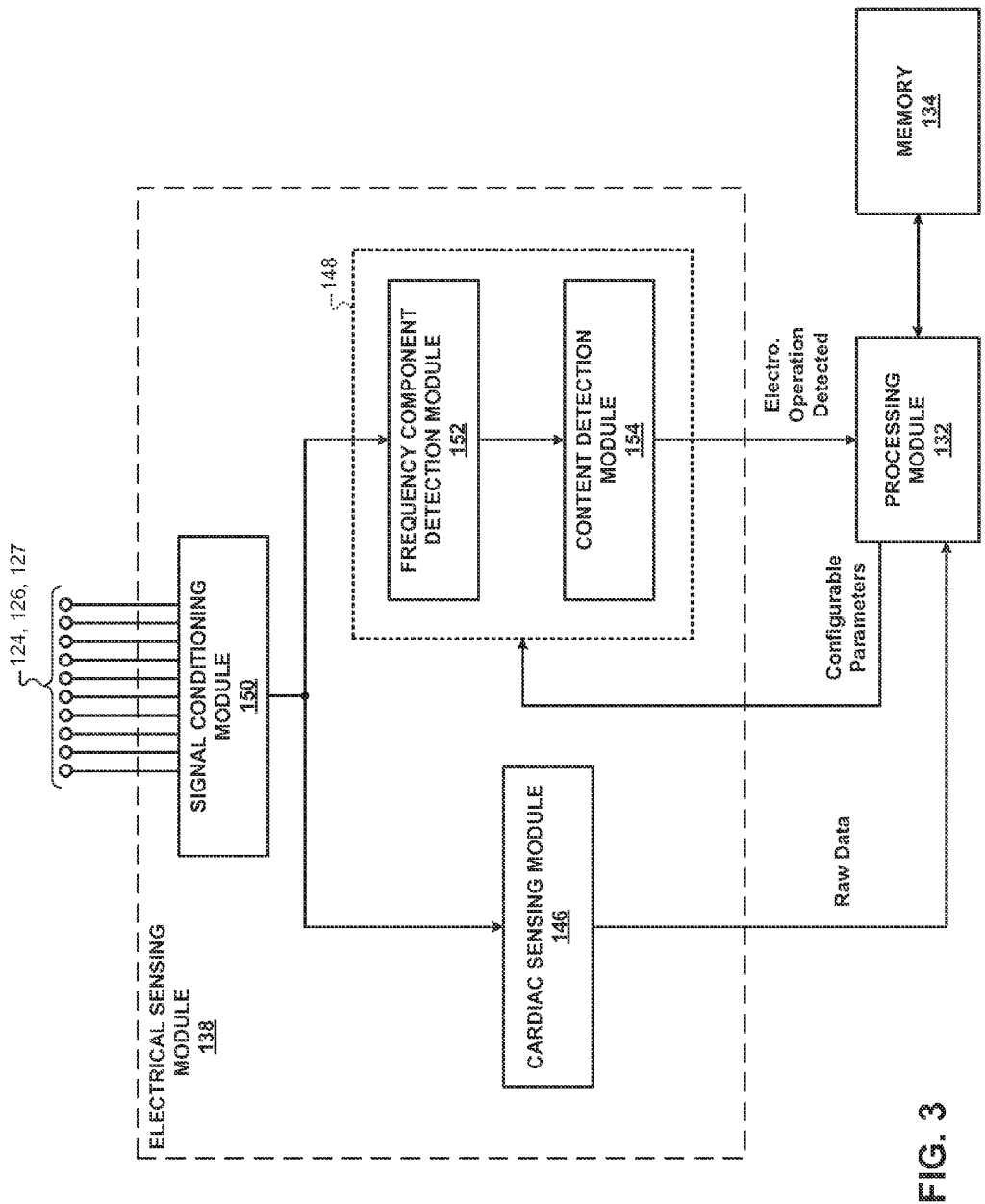
FIG. 3 is a functional block diagram of an example electrical sensing module included in the IMD of FIG. 2.

FIG. 3 is a functional block diagram that provides a more detailed view of an example electrical sensing module 138. Signal conditioning module 150, although not illustrated in FIG. 2, may be included in electrical sensing module 138 in some examples. Signal conditioning module 150 may acquire (i.e., receive) electrical signals via electrodes 124, 126, 127. In general, signal conditioning module 150 may acquire signals (e.g., voltage signals) via any combination of electrodes 124, 126, 127. Electrical signals received via electrodes 124, 126, 127 may include physiological signals and non-physiological signals. Physiological signals may include cardiac electrical signals or other physiological signals. Non-physiological signals may include electrosurgical noise in some examples. Other non-physiological noise may include common environmental noise, such as power line noise at 50-60 Hz.

Signal conditioning module 150 may perform signal conditioning operations on signals acquired via electrodes 124, 126, 127. In general, signal conditioning module 150 may acquire electrical signals via electrodes 124, 126, 127 and condition the signals such that cardiac sensing module 146 and electrosurgery detection module 148 are able to perform the functions attributed to modules 146, 148 described herein. In some examples, signal conditioning module 150 may amplify electrical signals acquired via electrodes 124, 126, 127. Additionally, or alternatively, signal conditioning module 150 may filter electrical signals acquired via electrodes 124, 126, 127.

Signal conditioning module 150 may output conditioned signals, e.g., amplified and/or filtered analog signals acquired via electrodes 124, 126, 127, to cardiac sensing module 146 and electrosurgery detection module 148. Although signal conditioning module 150 is illustrated as receiving electrical signals via electrodes 124, 126, 127, and outputting common signals to cardiac sensing module 146 and electrosurgery detection module 148, in some examples, signal conditioning module 150 may be absent from electrical sensing module 138. In these examples, cardiac sensing module 146 and electrosurgery detection module 148 may each have signal conditioning functionality, e.g., filtering and amplification functions. In summary, signal conditioning module 150 may generally represent signal conditioning functionality of electrical sensing module 138 that may be applied to signals acquired via electrodes 124, 126, 127 prior to operations performed on the acquired electrical signals by cardiac sensing module 146 and electrosurgery detection module 148.

Electrosurgery detection module 148 may receive the electrical signals acquired via electrodes 124, 126, 127, and may detect operation of electrosurgical device 107 based on analysis of the acquired electrical signals. As described above, electrosurgery detection module 148 may detect the presence of electrosurgical noise when the electrical signals acquired via electrodes 124, 126, 127 include greater than a threshold amount of signal content at a plurality of different frequency bands which typically do not include physiological electrical activity detected via electrodes 124, 126, 127 when electrosurgical device 107 is not in operation.

Electrosurgery detection module 148 includes a frequency component detection module 152 and a content detection module 154. Frequency component detection module 152 determines whether electrical signals acquired via electrodes 124, 126, 127 include a threshold amount of signal content in a plurality of different frequency bands. Content detection module 154 determines whether a threshold number of different frequency bands include a threshold amount of signal content. Content detection module 154 indicates to processing module 132 that operation of electrosurgical device 107 is detected when a threshold number of different frequency bands include signal content.

Processing module 132 may transition IMD 106 to a different mode of operation, referred to herein as a "safe operating mode," when operation of electrosurgical device 107 is detected. The safe operating mode may be an operating mode that prevents any operational issues that IMD 106 may potentially encounter when subjected to electrosurgical noise. In some examples, when IMD 106 includes pacing functionality, processing module 132 may transition IMD 106 to a safe operating mode, such as an asynchronous mode (e.g., VOO mode) so that electrosurgical noise may not cause inhibition of pacing. In some examples, when IMD 106 includes cardioverter-defibrillator functionality, processing module 132 may transition IMD 106 to a safe operating mode in which arrhythmia detection and arrhythmia therapy are disabled so that electrosurgical noise may not be interpreted as arrhythmias. The safe operating mode functionality may generally represent an operating mode that may be configured to prevent issues in an IMD in the presence of electrosurgical noise, and the details of the safe operating mode may depend on the functionality of the particular IMD and the issues involved with the IMD in the presence of electrosurgical noise. For example, it is contemplated that in other IMDs, such as neurostimulators, a safe operating mode may define settings that prevent potential issues with neurostimulators in the presence of electrosurgical noise.

Electrosurgical device 107 may be operated by a clinician in an intermittent fashion such that the clinician may operate electrosurgical device 107 for a period of time, and then turn off electrosurgical device 107 for another period of time. Based on this typical usage scenario, it is contemplated that electrosurgical noise may be presented to electrodes 124, 126, 127 intermittently. Electrosurgery detection module 148 may detect such intermittent use of electrosurgical device 107, and may indicate to processing module 132 that electrosurgical device 107 is in operation during the periods of time in which the clinician is operating electrosurgical device 107. In response to the indications from electrosurgery detection module 148, processing module 132 may intermittently enter and exit the safe operating mode in order to prevent issues from arising in IMD 106 in the presence of the intermittent electrosurgical noise.

In some examples, parameters of frequency component detection module 152 and content detection module 154 may be configurable. In these examples, processing module 132 may retrieve the configurable parameters from memory 134 and set the configurable parameters in frequency component detection module 152 and content detection module 154. As described above, the configurable parameters may be received from programmer 130 in some examples. In some examples, the configurable parameters may be selected by a clinician, or automatically determined by processing module 132, based on the general noise characteristics of the signals received from electrodes 124, 126, 127 when electrosurgical device 107 is not in operation. In these examples, a clinician, or processing module 132, may determine a typical power spectrum of signals received from 124, 126, 127 in the absence of operation of an electrosurgical device, and use the typical power spectrum to determine the threshold values for detection of electrosurgical device 107. For example, the configurable parameters may be set such that electrosurgical noise, and not typical electrical noise, may trigger the detection of the operation of electrosurgical device 107.

Figure 4:
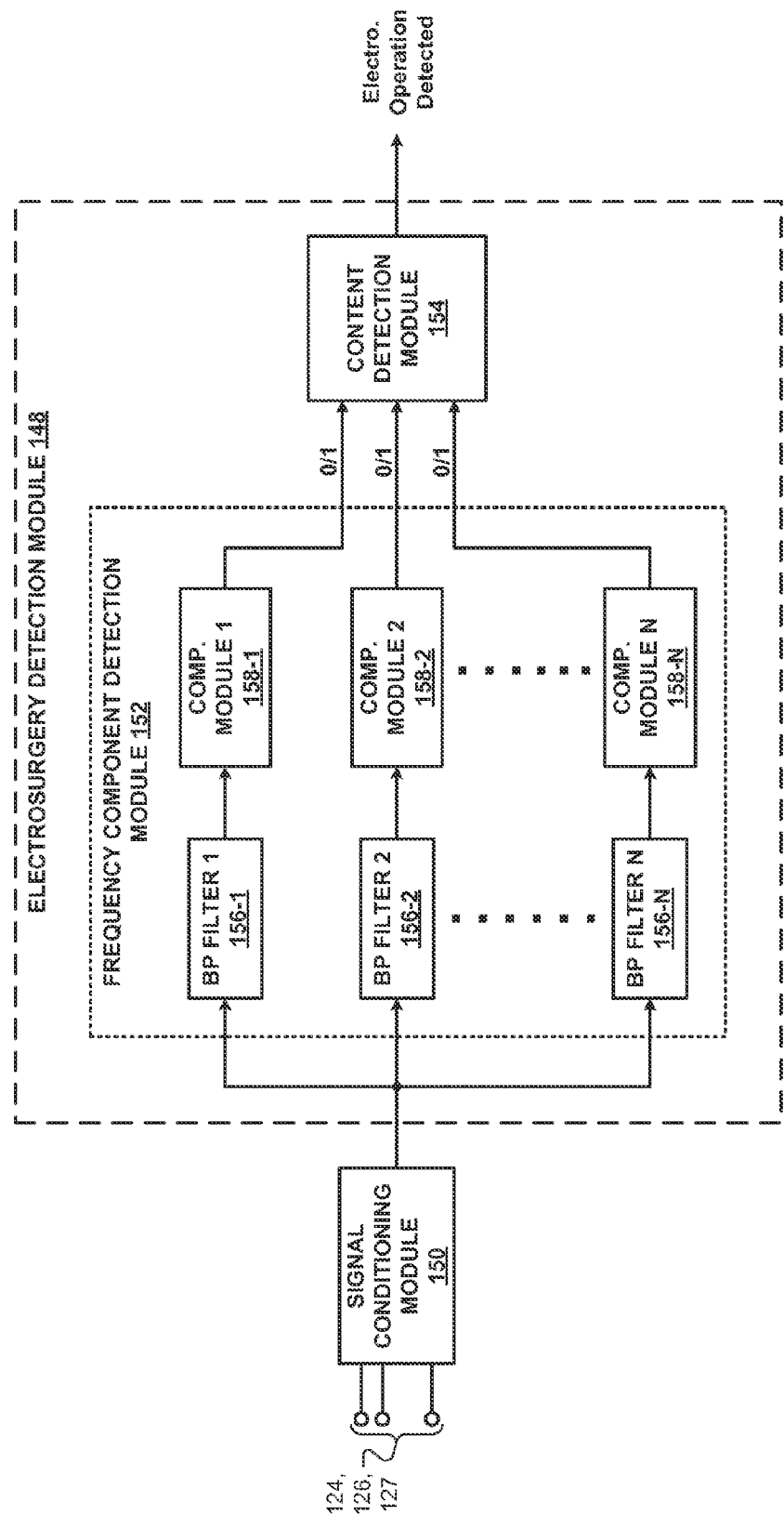
FIG. 4 shows a detailed view of an example electrosurgery detection module included in the electrical sensing module of FIG. 3.

FIG. 4 shows a detailed view of an example electrosurgery detection module 148. Frequency component detection module 152 includes a plurality of band-pass filters, 156-1, 156-2, . . . , and 156-N (referred to singly as "each band-pass filter 156," and collectively as "band-pass filters 156"). Additionally, frequency component detection module 152 includes a plurality of comparison modules 158-1, 158-2, . . . , and 158-N (referred to herein singly as "each comparison module 158," and collectively as "comparison modules 158"). Each band-pass filter 156 receives electrical signals (e.g., conditioned signals) acquired via electrodes 124, 126, 127. Each band-pass filter 156 may perform band-pass filtering operations on received signals. Each band-pass filter 156 may have a center frequency and may pass signals within a certain frequency range about that center frequency.

Each band-pass filter 156 may have different center frequencies. The bandwidth of each band-pass filter 156 may be similar or different. The center frequencies and bandwidths of band-pass filters 156 may be selected such that the passbands of band-pass filters 156 are separated from one another. Accordingly, band-pass filters 156 may pass signals having frequency ranges that are separated from one another. Although the passbands of band-pass filters 156 may be separated from one another, in some examples, the passbands of all band-pass filters 156 may not be separate, but instead, some of the passbands may overlap at the edges of the passbands.

The distances between the center frequencies of band-pass filters 156 and the widths of the passbands of band-pass filters 156 may be selected (e.g., set as factory defaults or programmable by a clinician) based on the expected frequency content of the electrosurgical noise and the expected frequency content of other electrical signals typically sensed by electrodes 124, 126, 127, such as physiological electrical signals and other electrical noise. As described above, electrosurgical noise may include high frequency content that may not be physiologically producible, may include a wide range of frequency content than may not be physiologically producible, and may include greater power at those frequencies which overlap with physiological electrical signals. The center frequencies of band-pass filters 156 and the widths of the passbands of band-pass filters 156 may be selected such that the outputs of band-pass filters 156 tend to include electrosurgical noise but tend not to include physiological electrical signals and other types of physiological and non-physiological noise other than electrosurgical noise. In other words, the center frequencies and the passbands of band-pass filters 156 may be selected such that the presence of signal components at the outputs of a plurality of band-pass filters 156 may likely indicate that electrosurgical noise has been acquired via electrodes 124, 126, 127.

Furthermore, as described above, electrosurgical noise may not only be differentiated from other electrical signals (e.g., physiological or non-physiological) based on frequency content, but electrosurgical noise may also be detected based on the power present in the electrosurgical noise within frequency bands that also include physiological signals. For example, in frequency bands that may include both electrosurgical noise and physiological signals, electrosurgical noise may generate a greater signal strength (e.g., power) than physiological electrical signals. Accordingly, in some examples, band-pass filters 156 may pass signals in frequency bands that also include physiological electrical signals, and electrosurgical noise may be detected based on the amount of signal content that is output from such band-pass filters 156, as described hereinafter.

Frequency component detection module 152 includes a plurality of comparison modules 158 that each receive filtered signals from respective band-pass filters 156. Each comparison module 158 may determine an amount of signal content included in the filtered signal received from the corresponding band-pass filter 156. For example, comparison module 158-1 may determine an amount of signal content included in the filtered signal received from band-pass filter 156-1, and comparison module 158-2 may determine an amount of signal content included in the filtered signal received from band-pass filter 158-2. Comparison modules 158 each determine whether a threshold amount of signal content is included in the filtered signals received from respective band-pass filters 156. Comparison modules 158 may indicate to content detection module 154 whether a threshold amount of signal content is included in filtered signals received from band-pass filters 156. The outputs of comparison modules 158 may be digital outputs (0/1) in that the outputs may indicate either that a threshold amount of signal content is included in the filtered signals received from band-pass filters 156 (1) or that a threshold amount of signal content is not included in the signals (0) received from band-pass filters 156. Content detection module 154 may then determine whether electrosurgical device 107 is in operation based on the outputs received from comparison modules 158.

As used herein, the "amount of signal content" included in a signal may refer to a quantitative measure of a signal. In some examples, the amount of signal content may refer to a quantified measure of a signal in the frequency domain, i.e., a quantified frequency domain parameter. For example, a quantified measure of a signal in the frequency domain may include a power of a signal in a frequency band. In other examples, the amount of signal content may refer to a quantified measure of a signal in the time domain. Example quantified measures of a signal in the time domain may include a quantified voltage parameter such as a peak value of a signal, a peak-to-peak value of a signal, an average value of a signal, etc.

Content detection module 154 may receive the outputs of each of comparison modules 158 and detect the presence of electrosurgical noise, i.e., determine whether electrosurgical device 107 is in operation, based on the outputs of each of comparison modules 158. Generally, content detection module 154 may determine that electrosurgical device 107 is in operation when a threshold number of comparison modules 158 indicate that a threshold amount of signal content is included in the filtered signals received from respective band-pass filters 156. A greater number of indications that a threshold amount of signal content is included in the filtered signals (i.e., more "1" values) may indicate that it is more probable that electrosurgical device 107 is in operation, since such indications may be consistent with electrosurgical noise that exhibits a power spectrum including a wide range of frequency content. A smaller number of indications that a threshold amount of signal content is included in the filtered signals (i.e., less "1" values) may indicate that it is less likely that electrosurgical device 107 is in operation since the presence of electrosurgical noise may tend to produce a power spectrum that would include a wider range of frequency content.

In some examples, content detection module 154 may include a threshold number that content detection module 154 uses to determine whether electrosurgical device 107 is in operation. The threshold number may generally indicate a threshold number of indications that may be required by content detection module 154 for content detection module 154 to determine that electrosurgical device 107 is in operation. For example, content detection module 154 may determine that electrosurgical device 107 is in operation when content detection module 154 receives a threshold number of indications that signal content is included in the filtered signals. Otherwise, content detection module 154 may determine that electrosurgical device 107 is not in operation when content detection module 154 receives less than a threshold number of indications that signal content is included in filtered signals.

The threshold number may be configurable, and may be programmed as factory settings, or programmed at a later time by a clinician using programmer 130. In some examples, the threshold number may be set to "2." In these examples, content detection module 154 may detect operation of electrosurgical device 107 if two or more of the N comparison modules 158 indicate a threshold amount of signal content. In other examples, the threshold number may be set to a value that is greater than 2. In still other examples, content detection module 154 may behave similar to an AND logic gate, and may require that all of the N comparison modules 158 indicate a threshold amount of signal content before content detection module 154 determines that electrosurgical device 107 is in operation. Content detection module 154 may indicate to processing module 132 when operation of electrosurgical device 107 is detected, and processing module 132 may then transition IMD 106 to a safe operating mode when operation of electrosurgical device 107 is detected, as described above.

Electrosurgery detection module 148 may include a variety of different configurable parameters that may be set as factory defaults or programmed by a clinician using programmer 130. In some examples, the threshold number used by content detection module 154 may be configurable, as described above. Additionally, the threshold amount of signal content used by comparison modules 158 may be programmable. Additionally, the filter characteristics of band-pass filters 156 may be configurable. For example, the center frequencies and the width of the passbands of band-pass filters 156 may be programmable.

Figure 5:
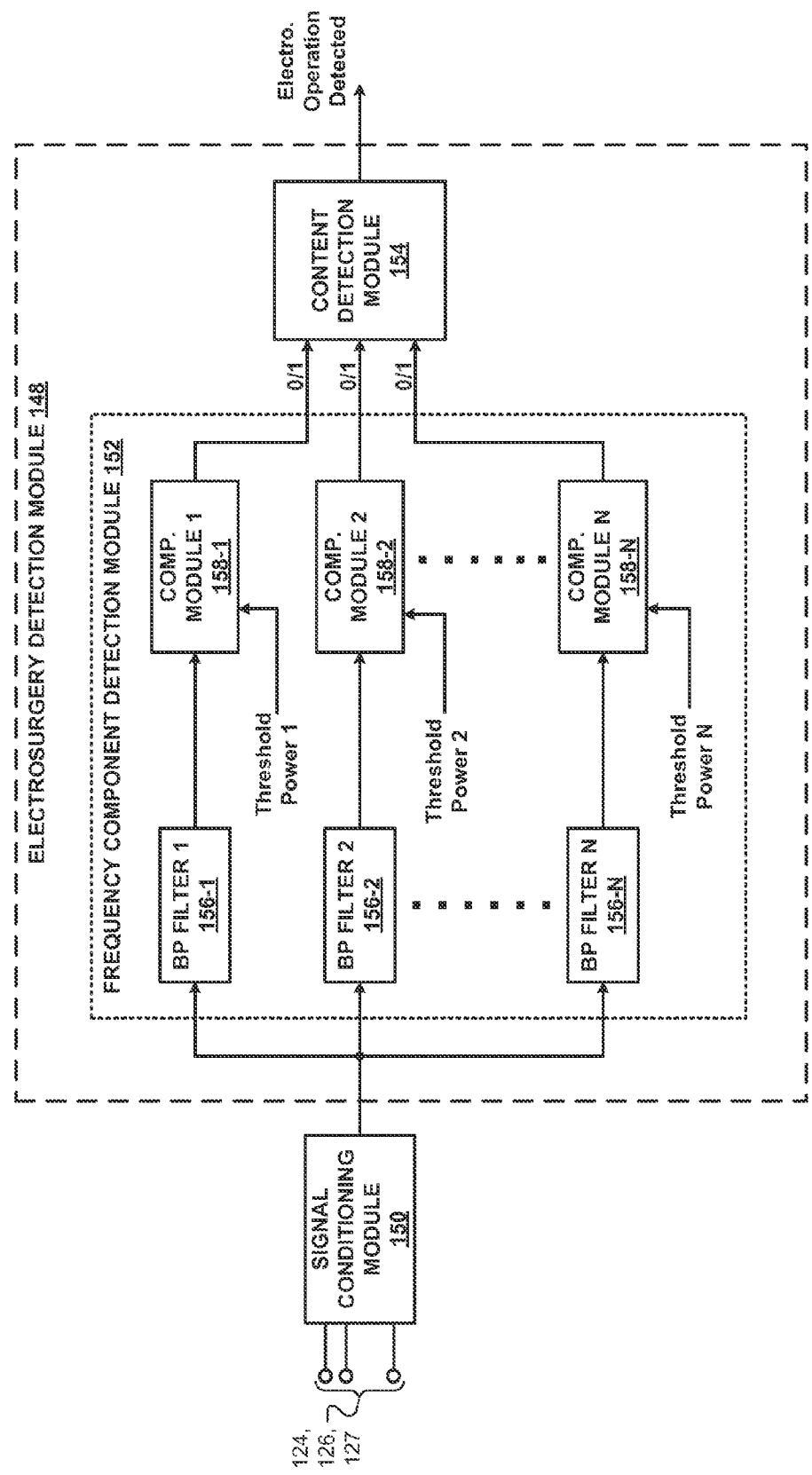
FIG. 5 shows a functional block diagram of an example frequency domain implementation of comparison modules included in the electrosurgery detection module of FIG. 4.
Figure 6:
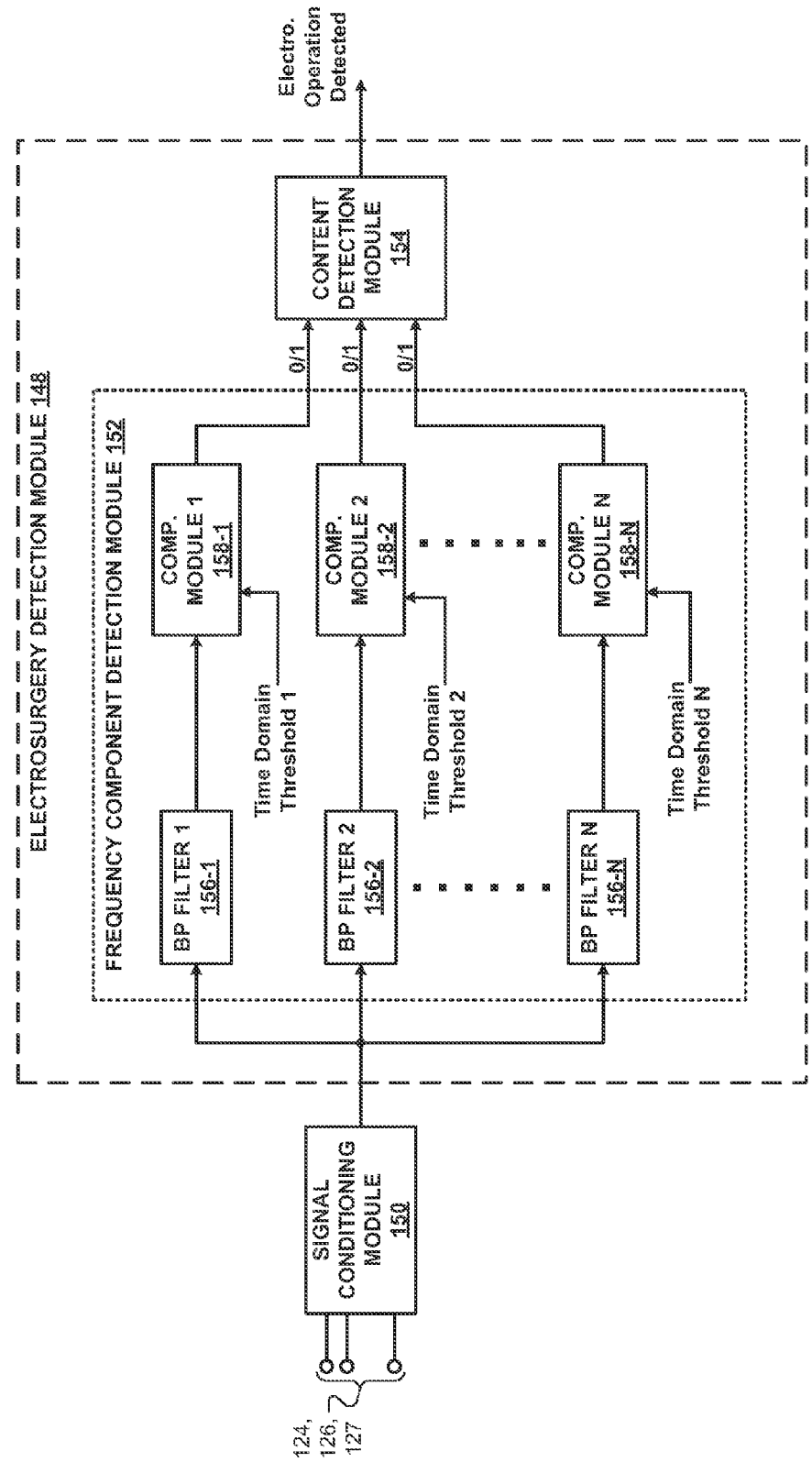
FIG. 6 shows a functional block diagram of an example time domain implementation of comparison modules included in the electrosurgery detection module of FIG. 4.

FIGS. 5-6 show different example implementations of electrosurgery detection module 148. FIG. 5 shows a functional block diagram of a frequency domain implementation of comparison modules 158. FIG. 6 shows a functional block diagram of a time domain implementation of comparison modules 158.

Referring now to FIG. 5, comparison modules 158 determine whether a threshold amount of signal content is included in the filtered signals in the frequency domain. In the example of FIG. 5, comparison modules 158 may determine the power of the filtered signals (e.g., using a Discrete Fourier Transform (DFT)) and then compare the determined power of the filtered signals to a threshold power value. Comparison modules 158 may determine that a threshold amount of signal content is included in the filtered signals when the determined power of the filtered signals is greater than the threshold power value. As illustrated in FIG. 5, each of comparison modules 158 may have an associated threshold power value (e.g., Threshold power 1, 2, . . . N) that comparison modules 158 may use to determine whether the threshold amount of signal content is included in the filtered signals. In some examples, the threshold power values associated with comparison modules 158 may be programmable. Although comparison modules 158 may determine the power of the filtered signals and compare the determined power to a threshold power value, in other examples, it is contemplated that comparison modules 158 may determine other parameters of the filtered signals in the frequency domain and compare those parameters to other thresholds in order determine whether a threshold amount of signal content is included in the filtered signals.

Referring now to FIG. 6, comparison modules 158 determine whether a threshold amount of signal content is included in the filtered signals in the time domain. In the example of FIG. 6, comparison modules 158 may determine a time domain parameter of the filtered signals (e.g., a voltage parameter such as a peak value, a peak-to-peak value, an average value, etc.) and then compare the determined time domain parameter to a time domain threshold, which may correspond to the determined time domain parameter (e.g., a peak value, a peak-to-peak value, an average value, etc.). Comparison modules 158 may determine that a threshold amount of signal content is included in the filtered signals when the determined time domain parameter of the filtered signals is greater than the time domain threshold. In some examples, comparison modules 158 may include voltage comparators that compare the filtered signals to a threshold voltage.

As illustrated in FIG. 6, each of comparison modules 158 may have an associated time domain threshold (e.g., Time domain threshold 1, 2, . . . N) that comparison modules 158 may use to determine whether the threshold amount of signal content is included in the filtered signals. In some examples, the time domain threshold values associated with comparison modules 158 may be programmable. Although comparison modules 158 may determine peak value, peak-to-peak-value, average value, etc., of the filtered signals, and compare the determined time domain value to a corresponding time domain threshold value, in other examples, it is contemplated that comparison modules 158 may determine other types of time domain parameters of the filtered signals and compare those parameters to other time domain thresholds in order determine whether a threshold amount of signal content is included in the filtered signals.

Figure 7:
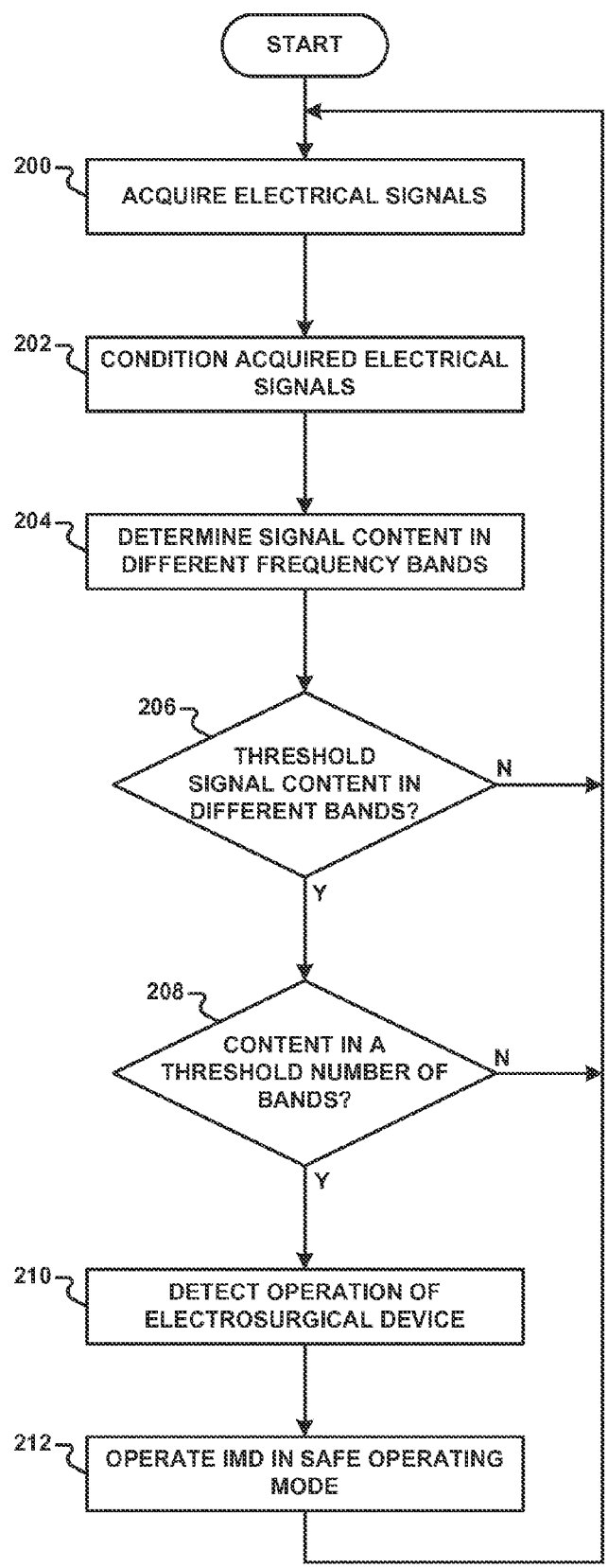
FIG. 7 shows an example method for detecting operation of an electrosurgical device.

FIG. 7 shows an example method for detecting operation of an electrosurgical device according to the present disclosure. Initially, signal conditioning module 150, when included in IMD 106, may acquire (i.e., receive) electrical signals via electrodes 124, 126, 127 (200). Signal conditioning module 150 may perform signal conditioning operations (e.g., amplification and/or filtering) on signals acquired via electrodes 124, 126, 127 (202). Signal conditioning module 150 may output conditioned signals, e.g., amplified and/or filtered analog signals acquired via electrodes 124, 126, 127, to frequency component detection module 152 (e.g., band-pass filters 156). Frequency component detection module 152 determines whether electrical signals acquired via electrodes 124, 126, 127 include a threshold amount of signal content in a plurality of different frequency bands (204). Frequency component detection module 152 may output digital values to content detection module 154 that indicate which bands of the plurality of different frequency bands include greater than a threshold amount of signal content. Content detection module 154 may then determine whether any of the plurality of different frequency bands includes signal content (206). If none of the plurality of different frequency bands include a threshold amount of signal content, then signal conditioning module 150 may continue to acquire signals via electrodes 124, 126, 127 in block (200).

If one or more of the plurality of different frequency bands include a threshold amount of signal content, content detection module 154 may determine whether a threshold number of frequency bands include a threshold amount of signal content (208). If less than a threshold number of frequency bands include a threshold amount of signal content, then signal conditioning module 150 may continue to acquire signals via electrodes 124, 126, 127 in block (200). If a threshold number of different frequency bands include a threshold amount of signal content, content detection module 154 may detect operation of electrosurgical device 107 (210). Content detection module 154 may then indicate to processing module 132 that operation of electrosurgical device 107 was detected, and processing module 132 may operate IMD 106 in a safe operating mode (212).

Although the IMD of the present disclosure is described above as picking up and detecting electrosurgical noise via electrodes, in some examples the IMD may additionally, or alternatively, detect electrosurgical noise using an internal antenna (e.g., a loop antenna or a serpentine antenna). For example, the IMD of the present disclosure may pick up electrosurgical noise via the internal antenna, detect the electrosurgical noise, and transition to the safe operating mode in order to prevent interpretation of the electrosurgical noise picked up by the electrodes as physiological electrical signals. The IMD may include one or more modules that receive the electrosurgical noise via the internal antenna and detect the received noise. For example, the IMD may include a module that includes functionality similar to that of electrosurgery detection module 148 described above. In this example, the IMD may detect electrosurgical noise in response to detection of a threshold amount of signal content picked up by the antenna in a threshold number of different frequency bands. In some examples, the module that detects electrosurgical noise via the antenna may monitor signal content at similar frequencies as electrosurgery detection module 148 that detects electrosurgical noise picked up by the electrodes. In other examples, the module that detects electrosurgical noise via the antenna may monitor signal content at different frequencies than electrosurgery detection module 148. For example, the module that detects electrosurgical noise via the antenna may monitor signal content of signals picked up in an RF frequency range while electrosurgery detection module 148 may monitor lower frequencies (e.g., approximately 10 Hz up to 20 kHz).

Various examples have been described. These and other examples are within the scope of the following claims.

What is claimed is:
1. A device comprising:
a plurality of electrodes configured to acquire an electrical signal in a patient; and
a detection module configured to:
determine whether the acquired electrical signal includes signal content greater than a threshold amount in each of N different frequency bands, wherein N is an integer that is greater than 1; and
detect operation of an electrosurgical device on the patient based on how many of the N different frequency bands include signal content greater than the threshold amount.

2. The device of claim 1, wherein the threshold amount of signal content is a quantified frequency domain parameter.

3. The device of claim 2, wherein the detection module is configured to determine a power of the signal in the one of the N frequency bands, wherein the threshold amount of signal content is a threshold power, and wherein the detection module is configured to determine that the acquired electrical signal includes signal content in the one of the N frequency bands when the determined power is greater than the threshold power.

4. The device of claim 1, wherein the threshold amount of signal content is a quantified voltage parameter.

5. The device of claim 4, wherein the quantified voltage parameter includes at least one of a peak voltage, a peak-to-peak voltage, an average voltage, and a root mean square voltage.

6. The device of claim 1, wherein the detection module is configured to:
determine the number of the N different frequency bands that include signal content greater than the threshold amount; and
detect operation of the electrosurgical device when greater than a threshold number of the N different frequency bands includes signal content greater than the threshold amount.

7. The device of claim 6, wherein the detection module is configured to detect operation of the electrosurgical device on the patient when two or more of the N different frequency bands include signal content greater than the threshold amount.

8. The device of claim 1, wherein the detection module is configured to:
detect operation of the electrosurgical device on the patient when all of the N different frequency bands include signal content greater than the threshold amount; and determine that the electrosurgical device is not operating on the patient when less than all of the N different frequency bands include signal content greater than the threshold amount.

9. The device of claim 1, wherein passbands of each of the N different frequency bands are separate from one another.

10. The device of claim 1, wherein the electrodes are configured to at least one of acquire cardiac electrical signals in the patient and provide cardiac electrical stimulation to the patient.

11. The device of claim 1, further comprising a processing module that is configured to:
detect an arrhythmia in the patient; and
disable detection of arrhythmias when the detection module detects operation of the electrosurgical device.

12. The device of claim 1, further comprising a processing module that is configured to:
control delivery of pacing pulses to a heart of the patient; and
transition to an asynchronous pacing mode when the detection module detects operation of the electrosurgical device.

13. The device of claim 1, wherein the threshold amount varies among the N different frequency bands.

14. A method comprising:
acquiring an electrical signal in a patient using a plurality of electrodes;
determining whether the acquired electrical signal includes signal content greater than a threshold amount in each of N different frequency bands, wherein N is an integer that is greater than 1; and
detecting operation of an electrosurgical device on the patient based on how many of the N different frequency bands include signal content greater than the threshold amount.

15. The method of claim 14, wherein the threshold amount of signal content is one of a quantified frequency domain parameter and a quantified voltage parameter.

16. The method of claim 14, further comprising:
determining the number of the N different frequency bands that include signal content greater than the threshold amount; and
detecting operation of the electrosurgical device when greater than a threshold number of the N different frequency bands includes signal content greater than the threshold amount.

17. The method of claim 14, further comprising at least one of:
disabling detection of arrhythmias in an implantable medical device (IMD) in response to detection of operation of the electrosurgical device; and
transitioning the IMD to an asynchronous pacing mode in response to detection of operation of the electrosurgical device.

18. The method of claim 14, wherein the plurality of electrodes are configured to be implanted in the patient.

19. The method of claim 18, wherein the plurality of electrodes are configured to at least one of acquire cardiac electrical signals in the patient and provide cardiac electrical stimulation to the patient.

20. The method of claim 14, wherein the threshold amount varies among the N different frequency bands.

21. A device comprising:
a plurality of electrodes configured to acquire an electrical signal in a patient;
N band-pass filters configured to filter the acquired electrical signal to generate N filtered signals, wherein N is an integer that is greater than 1;
N comparison modules, each configured to:
receive a different one of the N filtered signals; and
indicate whether the received signal includes greater than a threshold amount of signal content; and
a content detection module that detects operation of an electrosurgical device on the patient based on how many of the N comparison modules indicate that the received signal includes greater than a threshold amount of signal content.

22. The device of claim 21, wherein the threshold amount of signal content is a quantified frequency domain parameter.

23. The device of claim 22, wherein one of the N comparison modules is configured to determine a power of a received filtered signal, wherein the threshold amount of signal content is a threshold power, and wherein the one of the N comparison modules is configured to indicate that the received filtered signal includes greater than a threshold amount of signal content when the determined power is greater than the threshold power.

24. The device of claim 21, wherein the threshold amount of signal content is a quantified voltage parameter.

25. The device of claim 24, wherein the quantified voltage parameter includes at least one of a peak voltage, a peak-to-peak voltage, an average voltage, and a root mean square voltage.

26. The device of claim 21, wherein the content detection module is configured to:
determine the number of the N comparison modules that indicate that the received signal includes greater than a threshold amount of signal content; and
detect operation of the electrosurgical device when greater than a threshold number of the N comparison modules indicate that the received signal includes greater than a threshold amount of signal content.

27. The device of claim 21, further comprising a processing module that is configured to:
detect an arrhythmia in the patient; and
disable detection of arrhythmias when the content detection module detects operation of the electrosurgical device.

28. The device of claim 21, further comprising a processing module that is configured to:
control delivery of pacing pulses to a heart of the patient;
transition to an asynchronous pacing mode when the content detection module detects operation of the electrosurgical device.

29. The device of claim 21, wherein the threshold amount varies among the N different frequency bands.

* * * * *